US00PP27194P3

(12) United States Plant Patent
Helvick et al.

(10) Patent No.: US PP27,194 P3
(45) Date of Patent: Sep. 27, 2016

(54) ***LAGERSTROEMIA* PLANT NAMED 'PIILAG-VIII'**

(50) Latin Name: ***Lagerstroemia* sp. hybrid**
Varietal Denomination: PIILAG-VIII

(71) Applicant: Plant Introductions, Inc., Watkinsville, GA (US)

(72) Inventors: Rhonda Helvick, Madison, GA (US); Oren McBee, Bishop, GA (US); Mark Griffith, Watkinsville, GA (US); Jeff Beasley, Lavonia, GA (US); Michael A. Dirr, Bogart, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 103 days.

(21) Appl. No.: 14/121,502

(22) Filed: Sep. 12, 2014

(65) Prior Publication Data

US 2016/0081248 P1 Mar. 17, 2016

(51) Int. Cl.
*A01H 5/02* (2006.01)

(52) U.S. Cl.
USPC ..... Plt./252

(58) Field of Classification Search
USPC ..... Plt./252
See application file for complete search history.

*Primary Examiner* — June Hwu
(74) *Attorney, Agent, or Firm* — Lathrop & Gage LLP

(57) ABSTRACT

A new and distinct cultivar of *Lagerstroemia* plant named 'PIILAG-VIII', characterized by its compact, upright, intermediate growth habit, dark burgundy foliage that is planar, numerous large pink inflorescenes, resistance to powdery mildew and *Cercospora* leaf spot, and increase cold hardiness.

3 Drawing Sheets

Genus and species of plant claimed: *Lagerstroemia* sp. hybrid.

Variety denomination: 'PIILAG-VIII'.

BACKGROUND OF THE INVENTION

The present invention relates to a new and distinct cultivar of *Lagerstroemia* plant, botanically known as *Lagerstroemia* hybrid×L. 'Chocolate Mocha' (U.S. Plant Pat. No. 21,540), commonly known as crapemyrtle, and hereinafter referred to by the cultivar name 'PIILAG-VIII'. 'PIILAG-VIII' is grown primarily as an ornamental for landscape use.

'PIILAG-VIII' originated from open-pollinated seed of *Lagerstroemia* hybrid×L. 'Chocolate Mocha' (U.S. Plant Pat. No. 21,540) growing in Watkinsville, Ga. The cultivar 'PIILAG-VIII' originated in 2010 and was selected in a cultivated environment in Watkinsville, Ga. from the progeny of this open-pollination by continued evaluation for growth habit, foliage, flower, disease, and cold hardiness characteristics.

Asexual reproduction of 'PIILAG-VIII' by stem cuttings in Watkinsville, Ga. since 2011 has shown that all the unique features of this new *Lagerstroemia*, as herein described, are stable and reproduced true-to-type through successive generations of such asexual propagation.

SUMMARY OF THE INVENTION

Plants of the new cultivar 'PIILAG-VIII' have not been observed under all possible environmental conditions. The phenotype may vary somewhat with changes in light, temperature, soil and rainfall without, however, any variance in genotype.

The following traits have been repeatedly observed and are determined to be unique characteristics of 'PIILAG-VIII'. These characteristics in combination distinguish 'PIILAG-VIII' as a new and distinct cultivar: 1. Compact and tight, upright, intermediate growth habit; 2. Dark burgundy planar foliage in the summer; 3. Large rich pink flowers; 4. High resistance to powdery mildew and *Cercospora* leaf spot; 5. Increased cold hardiness.

Plants of 'PIILAG-VIII' differ from plants of the parent, *Lagerstroemia* hybrid×L. 'Chocolate Mocha' (U.S. Plant Pat. No. 21,540), primarily in flower color, size, and abundance, color and shape of the foliage, and growth habit. Plants of *Lagerstroemia* hybrid×L. 'Chocolate Mocha' (U.S. Plant Pat. No. 21,540) have pink flowers smaller in size and number of inflorescences, cupped foliage, green-purple summer leaf color, and an upright growth habit, where as plants of 'PIILAG-VIII' have larger richer pink blooms and more numerous inflorescences, the foliage is flatter, and the growth habit more upright and rigid.

'PIILAG-VII' can be compared to its sister seedling 'PIILAG-IV' (U.S. Plant Pat. No. 25,478). 'PIILAG-VII' has a dark burgundy planer foliage and large rich pink flowers, whereas 'PIILAG-IV' has curved dark maroon-purple foliage and has red flower buds that open to white flowers.

'PIILAG-VII' can be compared to 'PIILAG-V' (U.S. Plant Pat. No. 25,925) a sister seedling. 'PIILAG-VII' has planer dark-burgundy foliage whereas 'PIILAG-V' has curved dark-burgundy maroon foliage. 'PIILAG-VII' has large rich pink flowers and PIILAG-V has dark pink flowers.

BRIEF DESCRIPTION OF THE DRAWINGS

The accompanying color photographs illustrate the flower and foliage characteristics and the overall appearance of 'PIILAG-VIII', showing the colors as true as it is reasonably possible to obtain in color reproductions of this type. Colors in the photographs may differ slightly from the color values cited in the detailed botanical description which accurately describes the colors of the new *Lagerstroemia*.

DETAILED DESCRIPTION

Figure 1:
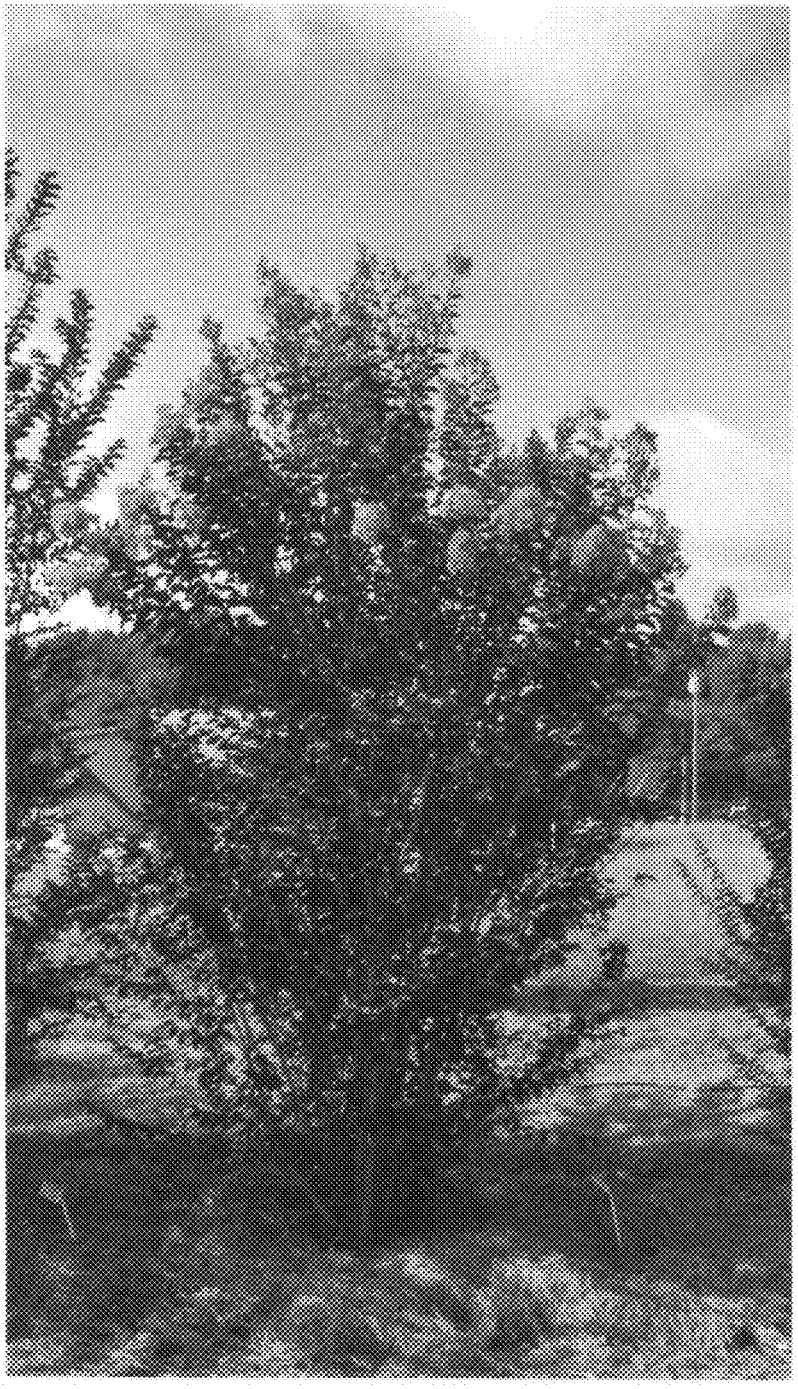
FIG. 1 illustrates the overall appearance of an established plant of a four-year-old 'PIILAG-VIII' planted in the ground.
Figure 2:
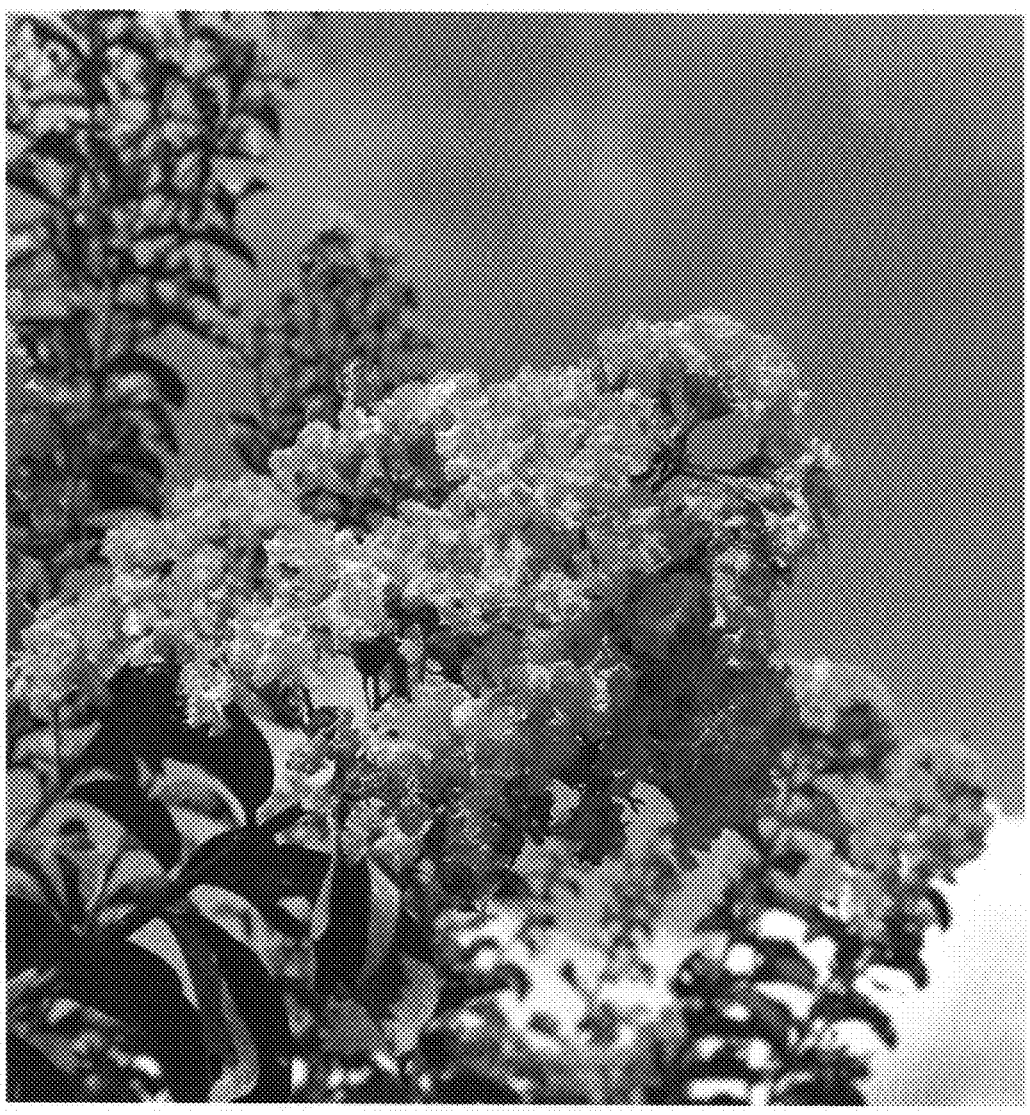
FIG. 2 illustrates a close-up view of the flower of a four-year-old 'PIILAG-VIII' plant.
Figure 3:
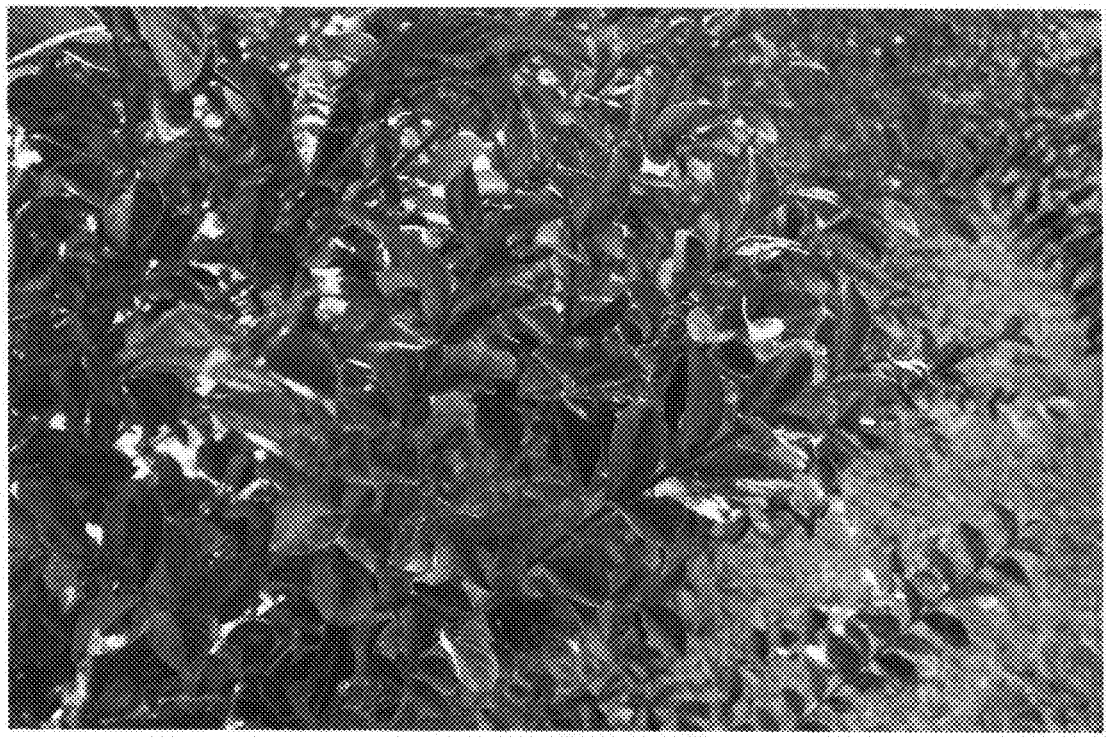
FIG. 3 illustrates a close up view of the foliage of a four-year-old 'PIILAG-VIII' plant.

In the following description, color references are made to The Royal Horticultural Society Colour Chart, 2007 Edition, except where general terms of ordinary dictionary significance are used. Plants used for the description were approximately two-years-old and were grown in 11.8 L containers under outdoor conditions in Watkinsville, Ga. Colors are described using The Royal Horticultural Society Colour Chart (R.H.S.).

Botanical classification: *Lagerstroemia* L., cultivar 'PIILAG-VIII'.

*Parentage*.—Female, or seed, parent: *Lagerstroemia* hybrid×L. 'Chocolate Mocha' (U.S. Plant Pat. No. 21,540). Male, or pollen parent: unknown (open-pollinated).

*Propagation*.—Terminal cuttings.

*Time to initiate roots, summer*.—About 21 days at 32° C.

Plant description: Flowering shrub; compact, upright, intermediate growth habit. Freely branching; lateral branches abundant without pruning, resulting in fine-textured, dense habit.

*Root description*.—Numerous, fine, fibrous and well-branched.

*Plant size*.—The original plant, now about four-years-old in the ground, is about 274 cm high from the soil level to the top of the uppermost inflorescences and about 188 cm wide. First year stems have a diameter of about 2.5 mm. First year stems have a length of 30 cm to 46 cm. Shape: squarish. Second year and older stems have a diameter of about 5 mm or more. Second year stems have a length of 61 cm to 91 cm. Shape: round.

*Trunk diameter*.—3 cm at the soil line. Color: 199B.

*Internode length*.—About 1.2 cm.

*Strength*.—Flexible when young, easily broken once mature.

*First year stem color* (*young*).—183A. Color (woody): N199C.

*Second year and older stem color*.—N199C.

*Bark*.—minor exfoliation in strips beginning on second or third year stems. Color of exfoliating bark: 199B. Average size 6.5 cm in length and 1.5 cm wide.

Vegetative buds: Sub-opposite to alternate in arrangement, imbricate, conical, with no pubescence.

*Color*.—183A.

*Size*.—About 2.5 mm in length and 1 mm in width.

Foliage description:

*Arrangement*.—Sub-opposite to alternate, simple. Length: about 4.2 cm. Width: about 2.5 cm. Shape: elliptical to ovate. Apex: acuminate. Base: cuneate. Margin: entire.

*Texture, upper surface*.—Matte with small amount of pubescence; lower surface: glossy.

*Venation pattern*.—Pinnate. Venation color of emerging foliage (upper and lower surfaces): 183A. Venation color of fully expanded foliage (upper and lower surfaces): 183A.

*Color in developing foliage* (*upper surface*).—N186C. Color in developing foliage (lower surface): N186C. Color in fully expanded foliage (upper surface): N137B. Color in fully expanded foliage (lower surface): N186C.

*Petiole length*.—About 2 mm. Petiole diameter: about 1 mm. Petiole color (upper and lower surfaces): 183A. Pubescence: none.

*Fall color*.—N186B, 187D or any combination of these colors.

Flower description: Flowers are produced from about June to September in Watkinsville, Ga. An inflorescence is showy for about two weeks, and individual flowers last about one day and are self-cleaning. Flowers are lightly fragrant.

*Inflorescence type*.—Panicle. Panicle contains between 50 to 150 buds and flowers. Inflorescence length: about 12 cm. Inflorescence width: about 10 cm.

*Peduncle*.—About 8.6 cm in length, about 2 mm in diameter, color is 183A, and no pubescence.

*Individual flowers*.—About 3 cm in height and 3 cm in diameter.

*Flower buds*.—Length: about 6 mm; Diameter: about 5 mm; Color: 181C. Unopened flower buds are globose with six distinct lines of dehiscence where they split to reveal the flower petals.

*Sepals*.—Arrangement/quantity: single whorl of six fused sepals. Length about 10 mm. Width: about 5 mm. Shape: elliptical. Apex: acute. Margin: entire. Texture, upper and lower surfaces: smooth, glabrous. Color when opening, upper surface: 183A. When opening lower surface: N144A. Fully opened, upper surface: 183A. Fully opened, lower surface: N144A.

*Pedicels*.—About 8 mm in length, 1 mm in diameter, 183A in color, and no pubescence.

*Calyx*.—About 8 mm in length, about 1 cm in diameter, 183A in color on both surfaces, and no pubescence.

Petals:

*Arrangement/appearance*.—Usually 6 or 7 per flower.

*Petal length*.—About 1.5 cm.

*Petal width*.—About 1.3 cm.

*Petal shape*.—Fan-shaped. Petal apex: ruffled, rounded. Petal base: sagittate. Petal margin: undulate. Petal texture (upper and lower surfaces): glabrous.

*Petal color*.—Upper and lower surfaces are 61 C.

Stamens:

*Quantity/arrangement*.—About 25 to 30 stamens clustered in the center, about 1.5 cm long, filament color is N155A, and anther color is 7A. The stamens are not pubescent.

*Pollen*.—Produced in moderate quantities and is 7A in color.

Pistils:

*Quantity*.—One superior pistil per flower.

*Pubescence*.—None.

*Pistil length*.—About 1.8 cm in length.

*Stigma shape*.—Round, about 1 mm in diameter.

*Stigma color*.—189A.

*Style color.*—45C and about 1.5 cm in length.

*Ovary color.*—2C and about 2 mm in diameter.

Fruit:

*Type/appearance.*—Six-valved, dehiscent, broad ellipsoidal capsule.

*Length.*—About 8 mm.

*Diameter.*—About 7 mm.

*Immature color.*—144C.

*Mature color.*—200C. Each capsule contains approximately 30 seeds that are about 5 mm long, 3 mm wide, and 200C in color.

Plant hardiness: Plant hardiness: USDA Hardiness Zone Map (2012): Zone 6 to 9.

Disease/pest resistance: Plants of the claimed *Lagerstroemia* variety grown in field and container trials have exhibited high resistance to powdery mildew and *Cercospora* leaf spot.

I claim:

1. A new and distinct *Lagerstroemia* plant named 'PIILAG-VIII', as illustrated and described herein.

* * * * *